United States Patent
Ramsey et al.

(10) Patent No.: US 11,099,914 B2
(45) Date of Patent: *Aug. 24, 2021

(54) CLOUD RULES AND ALERTING FRAMEWORK

(71) Applicant: CERNER INNOVATION, INC., Kansas City, KS (US)

(72) Inventors: Karen Ramsey, Lenexa, KS (US); Kristine Marie Nessa, University Heights, OH (US); Lynn Beverly Mader, Lenexa, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/298,845

(22) Filed: Mar. 11, 2019

(65) Prior Publication Data
US 2019/0205188 A1   Jul. 4, 2019

Related U.S. Application Data

(63) Continuation of application No. 15/796,151, filed on Oct. 27, 2017, now Pat. No. 10,248,475, which is a
(Continued)

(51) Int. Cl.
*G06F 9/54* (2006.01)
*G16H 40/63* (2018.01)
(Continued)

(52) U.S. Cl.
CPC ............. *G06F 9/542* (2013.01); *G16B 20/10* (2019.02); *G16H 10/60* (2018.01); *G16H 40/63* (2018.01); *G16H 40/67* (2018.01); *G16H 50/20* (2018.01)

(58) Field of Classification Search
CPC .. G06F 19/3418; G06F 19/3406; G06F 19/34; G16H 10/60
See application file for complete search history.

(56) References Cited

U.S. PATENT DOCUMENTS 5,190,313 A   3/1993   Hinkle
5,544,649 A   8/1996   David et al.
(Continued)

OTHER PUBLICATIONS

First Action Interview Office Action received for U.S. Appl. No. 15/796,151, dated Jun. 29, 2018, 5 pages.
(Continued)

*Primary Examiner* — Jeong S Park
(74) *Attorney, Agent, or Firm* — Shook, Hardy & Bacon LLP

(57) ABSTRACT

Systems, methods, and computer-readable media having computer-executable instructions embodied thereon for providing cloud rules and an alerting framework are provided. In embodiments, one or more rules associated with one or more healthcare information systems are received. The one or more rules each designate an initiating and at least one target application. One or more actions are associated to each target application. The initiating application is monitored for a trigger associated with the one or more rules. In embodiments, the trigger causes the one or more actions to be communicated to each target applications. In embodiments, the one or more actions initiate various changes in a display associated with each target application.

20 Claims, 8 Drawing Sheets

Related U.S. Application Data continuation of application No. 13/564,416, filed on Aug. 1, 2012, now Pat. No. 9,830,205.

(51) Int. Cl.
*G16H 10/60* (2018.01)
*G16B 20/10* (2019.01)
*G16H 50/20* (2018.01)
*G16H 40/67* (2018.01)

(56) References Cited

U.S. PATENT DOCUMENTS

| | | | |
|---|---|---|---|
| 7,945,589 B1 | 5/2011 | Weiss et al. | |
| 9,830,205 B2* | 11/2017 | Ramsey | G06F 9/542 |
| 10,248,475 B2* | 4/2019 | Ramsey | G16H 10/60 |
| 10,347,369 B1* | 7/2019 | Dudzinski | G06Q 50/22 |
| 2004/0199409 A1 | 10/2004 | Brown | |
| 2007/0139362 A1 | 6/2007 | Colton et al. | |
| 2008/0077436 A1 | 3/2008 | Muradia | |
| 2009/0177929 A1 | 7/2009 | Sijelmassi | |
| 2009/0281392 A1 | 11/2009 | Brown | |
| 2010/0010832 A1* | 1/2010 | Boute | G16H 10/60 705/3 |
| 2011/0208048 A1* | 8/2011 | Arima | A61B 6/467 600/436 |
| 2012/0278388 A1 | 11/2012 | Kleinbart et al. | |
| 2014/0310327 A1* | 10/2014 | Yip | G06F 9/52 709/201 |
| 2018/0101901 A1* | 4/2018 | Jones-McFadden | G06Q 40/02 |

OTHER PUBLICATIONS

Notice of Allowance received for U.S. Appl. No. 15/796,151, dated Nov. 19, 2018, 9 pages.

Preinterview First Office Action received for U.S. Appl. No. 15/796,151, dated Mar. 26, 2018, 4 pages.

* cited by examiner

CLOUD RULES AND ALERTING FRAMEWORK

CROSS-REFERENCE TO RELATED APPLICATIONS

This application is a continuation of U.S. patent application Ser. No. 15/796,151, filed Oct. 27, 2017, which is hereby incorporated by reference in its entirety.

BACKGROUND

In recent years, healthcare service providers have been making the transition from manual paper-based medical records to an electronic format. Commercially available computer software, such as PowerChart®, PowerChart Office®, and other Cerner Millennium® applications marketed by Cerner Corporation of Kansas City, Mo. have advanced the state of the art well beyond the conventional manual approach. Electronic-based records substantially increase the efficiency of healthcare providers and institutions. Electronic medical records also substantially reduce risks associated with high volumes of patient data and potential liabilities arising out of clerical errors or misinformation. The electronic format enhances communication between various providers and within institutions. As electronic clinical documentation continues to become increasingly prevalent, the variety of applications, electronic forms, electronic charts, and user interfaces, as well as the corresponding versatility of this format, continue to expand.

Many actions performed in various workflows for a particular department or area in a healthcare facility directly impact other workflows and need to be communicated to other teams and providers. Typically, this is addressed through alerts via text messaging, email, or direct manual communication. Unfortunately, these alerts are often overlooked because they are not embedded into the application utilized by each department of the healthcare facility. In many cases, such embedding is not even possible because different solutions, offerings, and systems are used by each department. Thus, there is no integration or adequate real-time communication between departments and direct impact of the display of a particular application based on a rule or trigger by another cannot be achieved.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to systems, methods, and computer-readable media having computer-executable instructions embodied thereon for performing a method in a computerized healthcare system to provide a cloud rules and alerting framework. In one embodiment, one or more computer storage media having computer-executable instructions embodied thereon, that when executed by one or more computing devices, cause the one or more computing devices to perform a method of providing cloud rules and an alerting framework. The method includes receiving one or more rules associated with one or more healthcare information systems. The one or more rules each designate an initiating and at least one target application. One or more actions are associated to the at least one target application. The initiating application is monitored for a trigger associated with the one or more rules.

In one embodiment, a system for providing cloud rules and an alerting framework is provided. The system comprises a processor coupled to a computer-storage medium, the computer-storage medium having stored thereon a plurality of computer software components executable by the processor. The computer software components include a rule component for receiving one or more rules associated with one or more healthcare information systems. The one or more rules each designate an initiating and at least one target application. An association component associates one or more actions to the at least one target application. A monitoring component monitors the initiating application for a trigger associated with the one or more rules. A trigger component receives the trigger associated with the one or more rules. A communication component communicates the one or more actions to the at least one target application.

In one embodiment, one or more computer storage media having computer-executable instructions embodied thereon, that when executed by one or more computing devices, cause the one or more computing devices to perform a method for providing cloud rules and an alerting framework. The method includes subscribing a target application to an alerting framework. The alerting framework includes one or more rules. One or more actions are configured to execute on the target application when the target application receives communication from the alerting framework that the one or more rules are satisfied. The one or more actions are executed on the target application.

BRIEF DESCRIPTION OF THE SEVERAL VIEWS OF THE DRAWINGS

The present invention is described in detail below with reference to the attached drawing figures, wherein:

FIGS. 5A-7B are illustrative screen displays illustrating various changes in displays associated with various target applications, in accordance with embodiments of the present invention.

DETAILED DESCRIPTION

Figure 1:
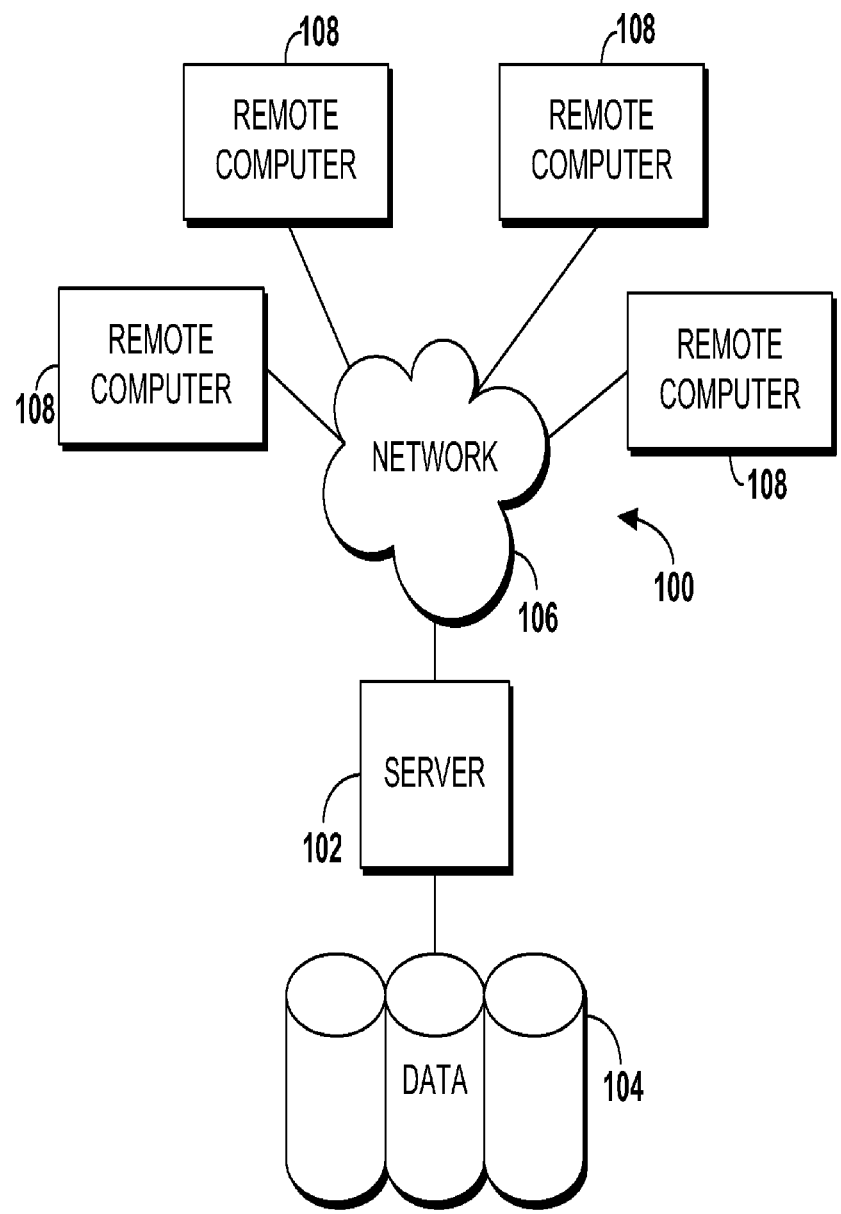
FIG. 1 is a block diagram of an exemplary computing system suitable for use in implementing embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide systems, methods, and computer-readable media having computer-executable instructions embodied thereon for providing cloud rules and an alerting framework. An exemplary operating environment is described below, though one of ordinary skill in the art will appreciate that other suitable operating environments may be used.

Having briefly described embodiments of the present invention, an exemplary operating environment suitable for use in implementing embodiments of the present invention is described below. Referring now to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. Embodiments of the present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and non-volatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22. For example, the database cluster 24 can contain electronic clinical documents capable of receiving multiple types of input, including images, dictation audio input, structured user input, free-text input, and system-generated input. Database cluster 24 can contain electronic medical records for various patients. Data from these records can be used by the system to generate system-generated input to be received as a trigger into an alerting framework. And, electronic clinical documents that have been populated with various forms of input can be stored in database cluster 24.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, image capturing devices, microphones, satellite dishes, scanners, or the like. Commands and information may be sent directly from a remote healthcare device to the server 22. In accordance with various embodiments of the present invention, commands and information may also be sent directly from an image capturing device to the server 22, and vice versa. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnections are well known. Accordingly, additional details concerning the internal construction of the server 22 and the remote computers 28 are not further disclosed herein.

The electronic clinical document can be provided via any type of graphical display, such as a computer monitor or any other type of graphical presentation apparatus, such as for example, an LCD screen, a laptop display, or a handheld PDA device. An electronic clinical document can be any type of electronic medical documentation relevant to a particular patient or area of the healthcare facility and can be part of an electronic healthcare information technology system. An electronic clinical document can also be a clinical event document relating to a particular clinical event for a patient, including, by way of example only, a patient visit or encounter. By way of example and not limitation, electronic clinical documents may be images, clinical notes, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information. Electronic clinical documents may be stored within an overall electronic medical chart or electronic medical record associated with a patient.

The format for electronic clinical documents may be customized by the user and/or may be established by a particular healthcare institution, such as by using a profile stored in a database, such as database cluster 24, or by using a locally stored profile on a remote computer (e.g., remote computer 28 of FIG. 1).

Figure 2:
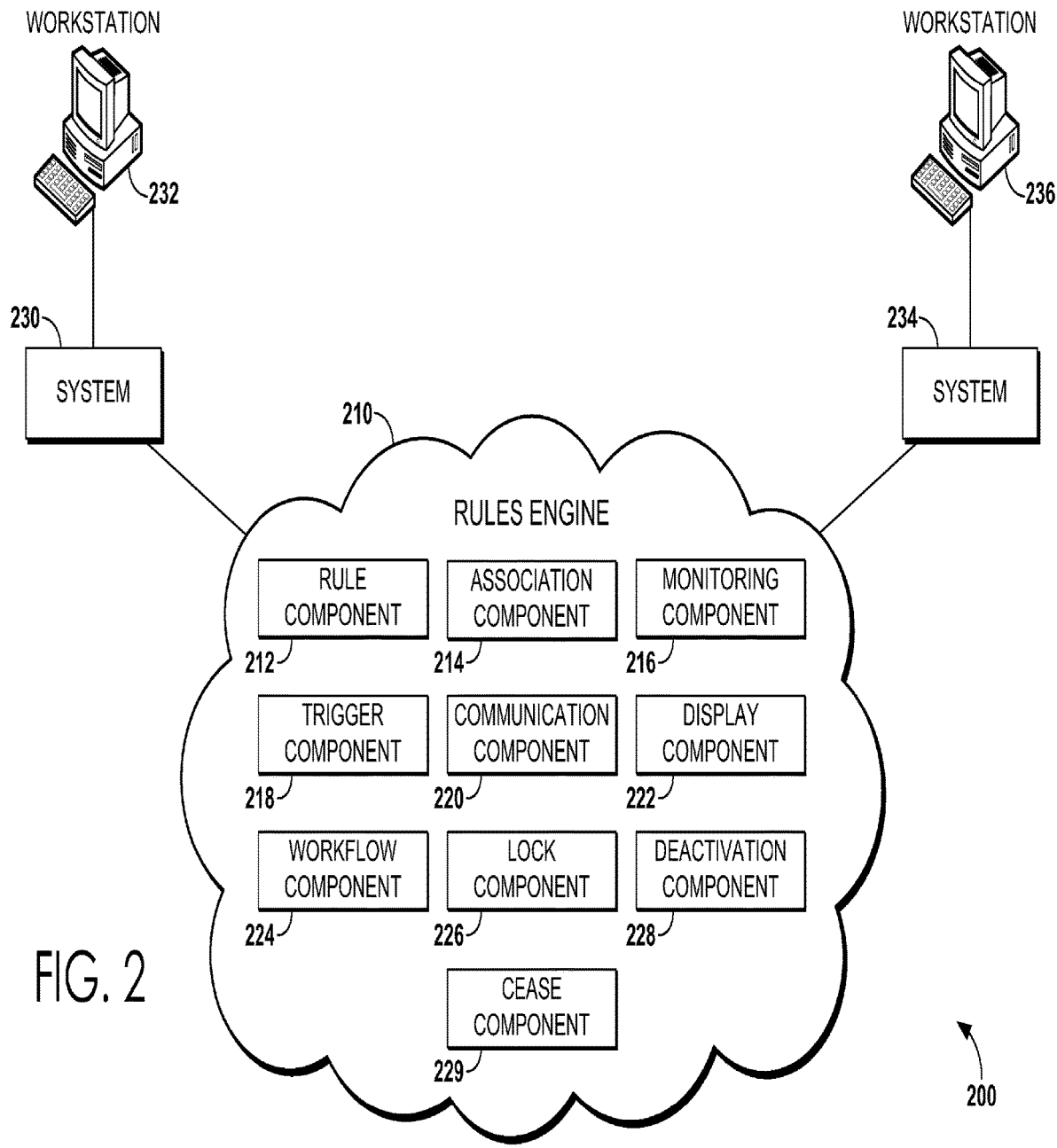
FIG. 2 schematically shows a network environment suitable for performing embodiments of the invention.

Referring now to FIG. 2, a block diagram is provided illustrating an exemplary system 200 in which an alerting framework 210 is shown communicatively coupled, such as via a network, to two healthcare information systems 230, 234, in accordance with an embodiment of the present invention. Each healthcare information system 230,234 is communicatively coupled, such as via a network, to remote computers 232,236. It should be understood that any number of healthcare information systems can be connected to the alerting framework 210. It should also be understood that any number of remote computers 232,236 can be connected to each healthcare information system 230,234. The alerting framework 210, the healthcare information systems 230, 234, and the remote computers 232,236 may be part of a comprehensive computing system within a clinical environment similar to the exemplary computing system 20 discussed above with reference to FIG. 1.

The alerting framework 210 may include a database (not shown) storing data communicated by the healthcare information systems 230,234 and the remote computers 232,236. Each healthcare information system 230,234 may also include a database (not shown) storing data communicated by the remote computers 232,236 or various medical devices (not shown). The alerting framework 210 is comprised of various components, including rule component 212, association component 214, monitoring component 216, trigger component 218, and communication component 220. In various embodiments, the alerting framework 210 includes display component 22, workflow component 224, lock component 226, deactivation component 228, cease component 229.

Rule component 212 receives one or more rules associated with one or more healthcare information systems. The one or more rules each designate an initiating and at least one target application. For example, the initiating application may be system 230 and the target application may be system 234. In addition to designating the initiating application, the one or more rules may establish a condition, setting, or threshold that must be met by the initiating application. In this respect, the condition, setting, or threshold corresponds to a trigger associated with the one or more rules.

Association component 214 associates one or more actions to the at least one target application. The one or more actions correspond to actions the target application takes when the condition, setting, or threshold is met by the initiating application. In one embodiment, the one or more actions initiates a change in a display associated with the at least one target application. In one embodiment, the change in display is a change in the background color of the at least one target application. In one embodiment, the change in display causes the at least one target application to flash a specific color or icon on the display. In one embodiment, the one or more actions initiate custom changes to each target application. In one embodiment, the one or more actions initiates a change in a workflow associated with the at least one target application. In one embodiment, the one or more actions cause the at least one target application to be locked until corrective action is taken.

Monitor component monitors 216 the initiating application for a trigger associated with the one or more rules. The trigger indicates that the condition, setting, or threshold has been met by the initiating application. Trigger component 218 receives the trigger associated with the one or more rules. Communication component 220 communicates the one or more actions to the at least one target application.

In one embodiment, display component 222 changes a display for the at least one target application. For example, in one embodiment, display component 222 changes the background color of the at least one target application to immediately captures the attention of and alerts the responsible clinician. In another embodiment, display component 222 causes the at least one target application to flash a specific color, icon, or text on the display.

In one embodiment, workflow component 224 initiates a change in a workflow associated with the at least one target application. This causes display component 222 to display a modified workflow associated with the at least one target application that is based on the condition, setting or threshold met by the initiating application.

In one embodiment, lock component 226 locks the at least one target application until corrective action is taken. This prevents a clinician from taking any action within the target application other than one that corrects the current condition, setting, or threshold that has been met by the initiating application. Such corrective action may be simply charting a particular item within the target application. Or the corrective action may require the clinician to administer, order, or dispense a particular medication or treatment to the patient.

In one embodiment, deactivation component 228 receives a deactivation trigger for the one or more rules. In one embodiment, the deactivation trigger indicates that the condition, setting, or threshold is no longer met by the initiating application. In another embodiment, the deactivation trigger indicates that the appropriate corrective action has been taken by the at least one target application. It should be appreciated that a deactivation trigger may be received for only one of the at least one target applications. For example, when corrective action is required, one of the at least one target applications may satisfy this requirement before another. Thus, the one that has already satisfied the requirement may communicate the deactivation trigger to deactivation component 228. Once the deactivation trigger is received by deactivation component 228, cease component 229 communicates to the at least one target application to cease the one or more actions.

Figure 3:
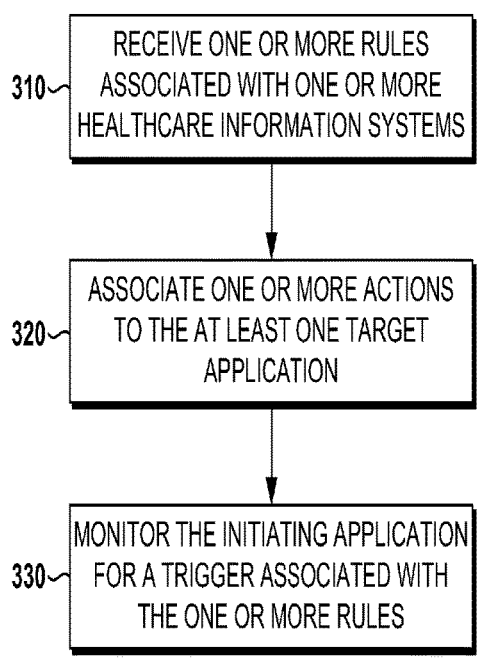
FIG. 3 is a flow diagram showing an exemplary method for providing cloud rules and an alerting framework, in accordance with an embodiment of the present invention.

With reference to FIG. 3, an exemplary flow diagram representative of a method for providing cloud rules and an alerting framework in accordance with an embodiment of the present invention is shown and referenced generally by reference numeral 300. Method 300 may be implemented using the above-described exemplary computing system environment (FIG. 1) and, by way of example only, may be utilized by a healthcare facility to communicate alerts across all healthcare information systems supporting a particular patient. The terms "individual", "person", and "patient" are used interchangeably herein and are not meant to limit the nature of the referenced individual in any way. Rather, the methods and systems described herein are equally applicable in, for instance, a veterinary setting.

Initially, as shown at step 310, one or more rules associated with one or more healthcare information systems is received. The one or more rules each designate an initiating and at least one target application. One or more actions are associated, at step 320, to the at least one target application. At step 330, the initiating application is monitored for a trigger associated with the one or more rules. The trigger corresponds to a condition, setting, or threshold in the initiating application. When the condition, setting, or threshold is met, the initiating application communicates the trigger to the alerting framework.

In one embodiment, a trigger associated with the one or more rules is received. Once the trigger is received, the alerting framework identifies the one or more rules associated with the trigger. The alerting framework also identifies the one or more actions associated to the at least one target application. In one embodiment, the one or more actions are communicated to the at least one target application.

In one embodiment, the one or more actions initiates a change in a display associated with the at least one target application. In one embodiment, the change in display is a change in the background color of the at least one target application. In one embodiment, the change in display causes the at least one target application to flash a specific color or icon on the display. In one embodiment, the one or more actions initiate custom changes to each target application. The custom changes allow a user of a particular target application to tailor the change in display to that target application, such that the change in display is noticeable to the user. In this respect, the one or more actions may be different for each target application.

In one embodiment, the one or more actions initiates a change in a workflow associated with the at least one target application. The change in the workflow allows a clinician to promptly provide the proper care for a patient. For example, the clinician may be instructed to document more or less frequently or may be instructed to administer or order a medication. The change in the workflow also is important to the healthcare facility for reimbursement purposes. For example, if a patient receives a particular treatment, workflows must be followed properly in order for the healthcare facility to receive full reimbursement for that treatment. The alerting framework provides a persistent change in the visual presentation of other associated systems across the healthcare facility.

In one embodiment, the one or more actions cause the at least one target application to be locked until corrective action is taken. This forces a clinician responsible for the target application to take corrective action before any additional action can be taken within the target application. Such corrective action may be to acknowledge an alert, order or administer a medication, document information, or perform an action corresponding to the workflow or a change in the workflow.

In one embodiment, a deactivation trigger for the one or more rules is received. In one embodiment, the alerting framework communicates to the at least one target application to cease the one or more actions. Thus, as can be appreciated, the alerting framework provides a persistent change to the at least one target application until the deactivation trigger is received. The deactivation trigger is received, in one embodiment, when the initiating application communicates to the alerting framework that the condition, setting, or threshold within the initiating application is no longer met. In another embodiment, the deactivation trigger is received when a corresponding action is taken on one of the at least one target applications. In another embodiment, the deactivation trigger is received when all corresponding actions are taken an all of the at least one target applications.

Figure 4:
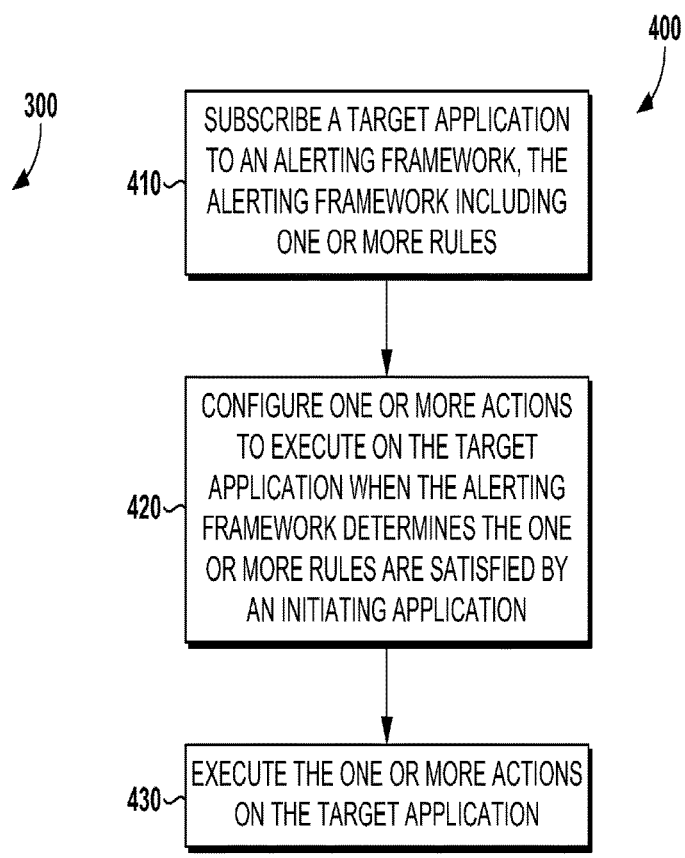
FIG. 4 is a flow diagram showing an exemplary method for providing cloud rules and an alerting framework, in accordance with an embodiment of the present invention.
Figure 5A:
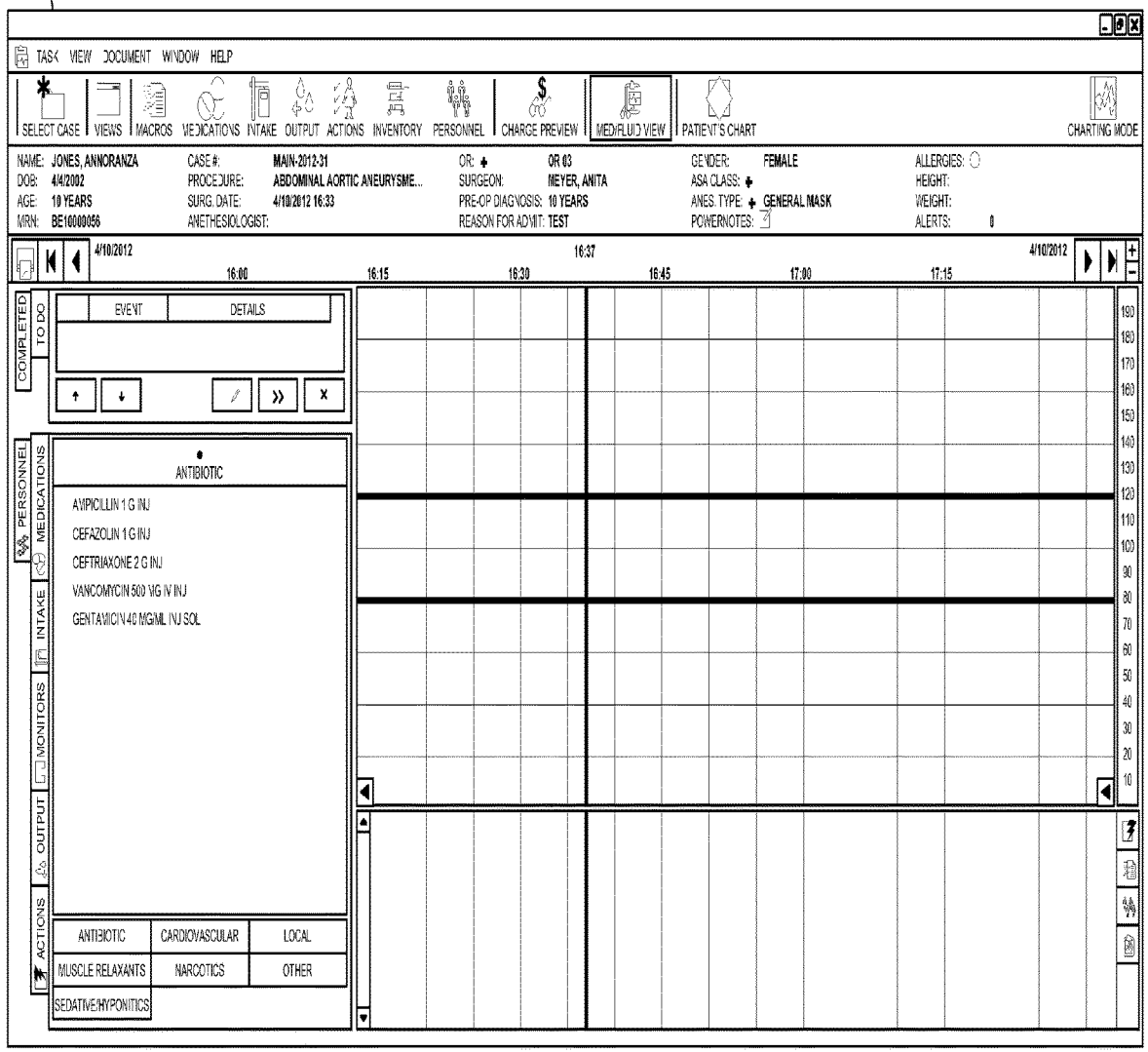
Figure 5B:
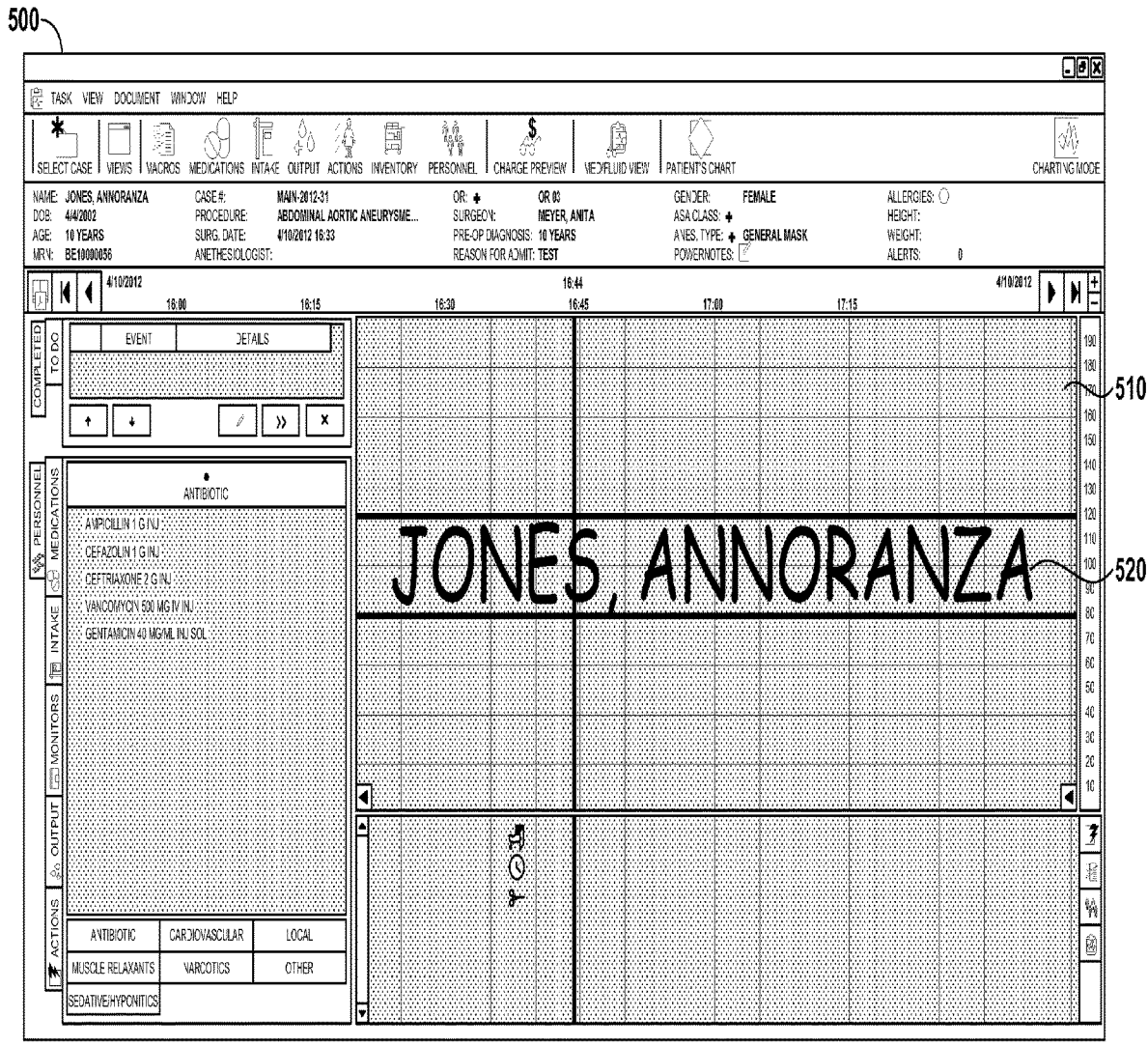
Figure 6A:
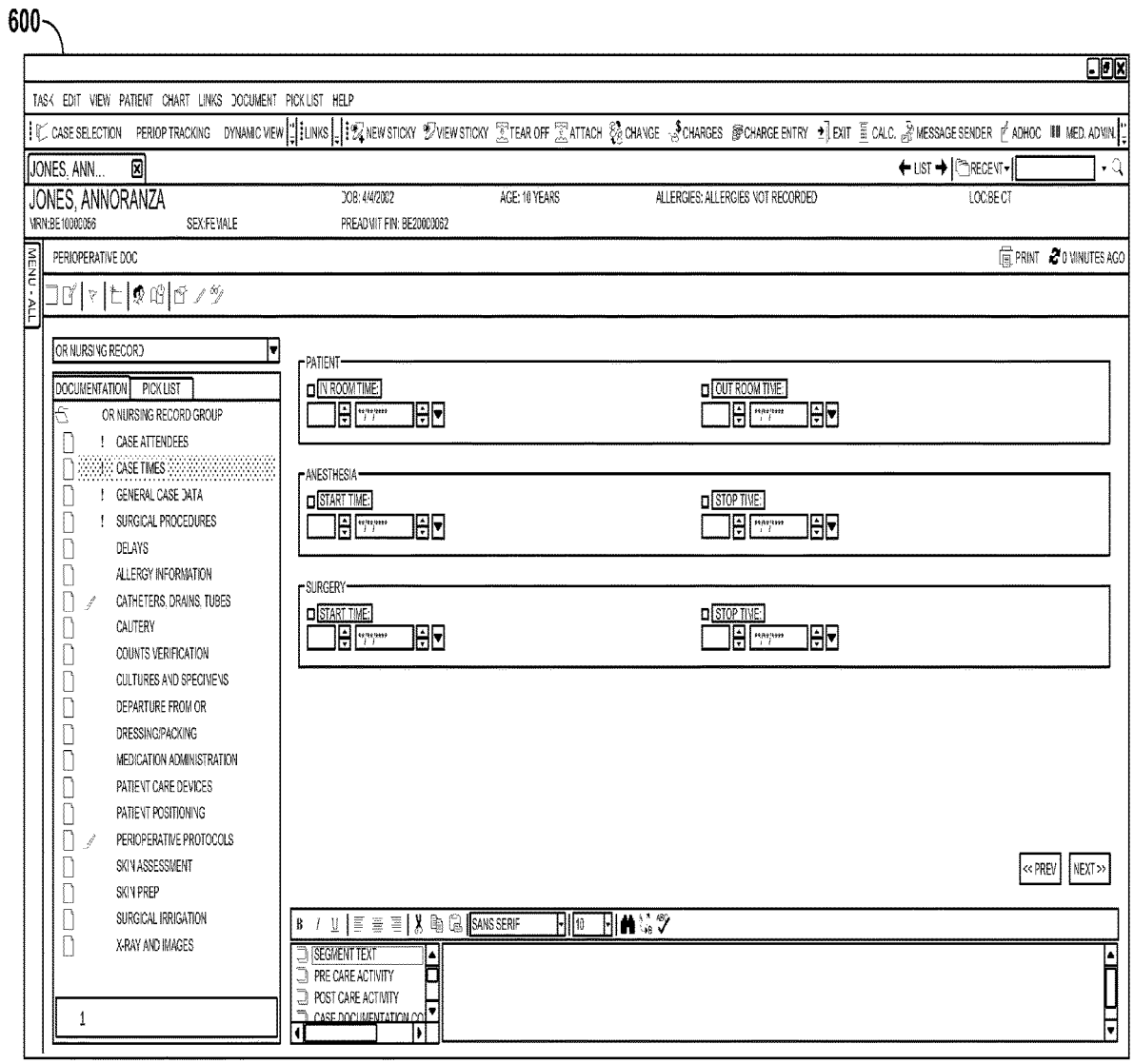

Referring now to FIG. 4, an exemplary flow diagram representative of a method for providing cloud rules and an alerting framework in accordance with an embodiment of the present invention is shown and referenced generally by reference numeral 400. Method 400 may be implemented using the above-described exemplary computing system environment (FIG. 1) and, by way of example only, may be utilized for protocol driven image acquisition.

Initially, as shown at step 410, a target application subscribes to an alerting framework. The alerting framework includes one or more rules. The one or more rules correspond to a condition, setting, or threshold in an initiating application. One or more actions to execute on the target application are configured at step 420, when the target application receives communication from the alerting framework that the one or more rules are satisfied. The one or more actions are executed, at step 430, on the target application.

In one embodiment, the one or more actions initiate a change in a display associated with the target application. In one embodiment, the one or more actions initiate a change in a workflow associated with the target application. In one embodiment, the target application receives a notification that the alerting framework received a deactivation trigger and the one or more actions are ceased on the target application.

Referring now to FIGS. 5A-7B, illustrative screen displays 500,600,700 illustrate various changes in displays associated with various target applications, in accordance with embodiments of the present invention. For example, a typical anesthesia record, a typical nursing record, and a typical perioperative tracking display for a patient about to be connected to a cardiac pump is displayed in FIGS. 5A, 6A, and 7A, respectively. Once the surgeon connects the pump to the patient and the perfusionist starts the bypass machine, a trigger is generated. The trigger can be generated from the bypass machine itself or in accordance with documentation by the perfusionist. This trigger is received by the alerting framework and communicated to associated systems. The anesthesia system subscribes to this alert because once the patient is on the pump, the anesthesiologist no longer ventilates the patient since the perfusionist is already oxygenating the patient's lungs via the pump. So the anesthesia system is configured to change the display 500 accordingly, as illustrated by FIG. 5B. In this example, the background 510 of the display changes color and the patient's name 520 is prominently displayed across the screen so the anesthesiologist is immediately aware of the patient's condition.

Figure 6B:
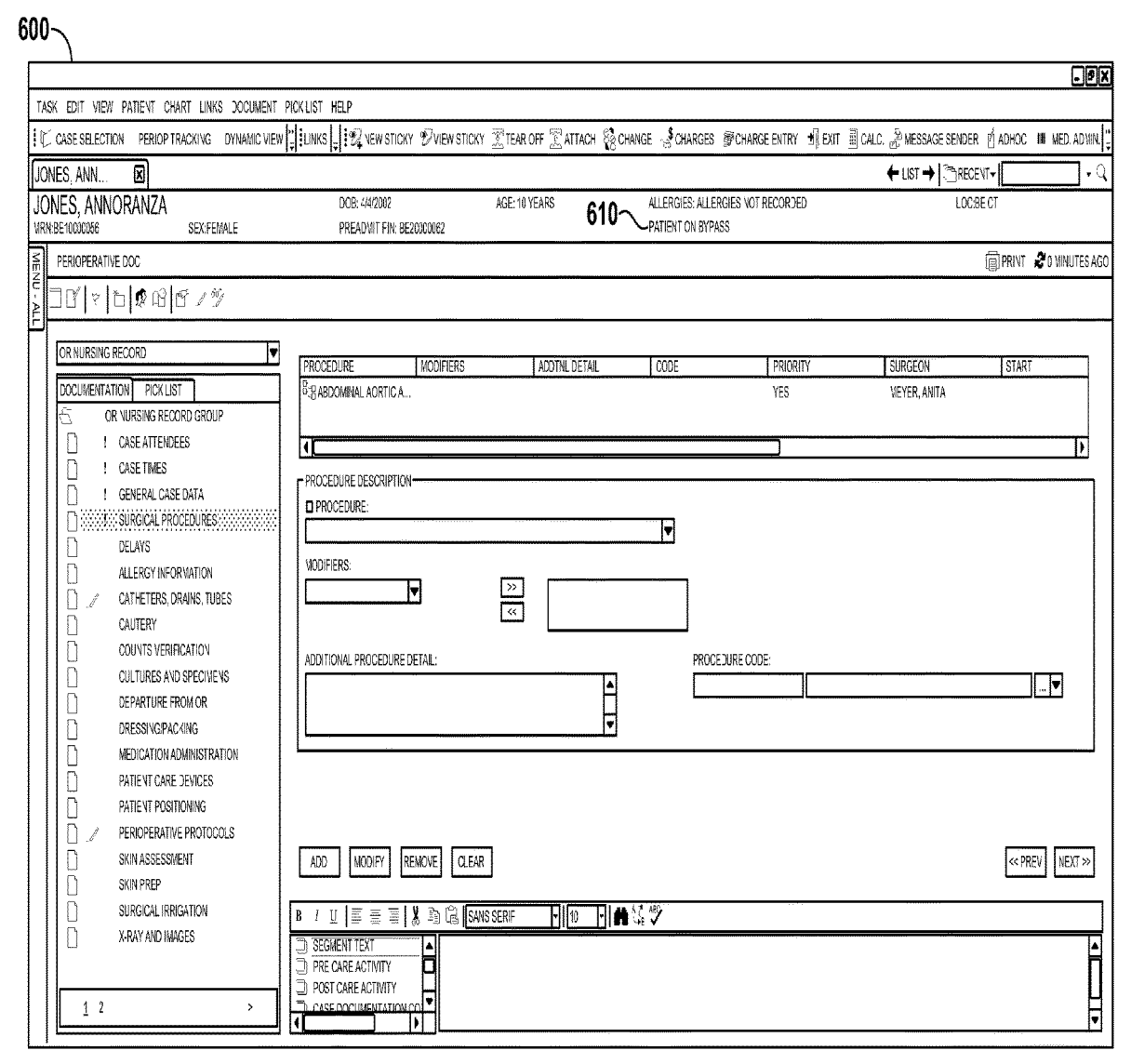
Figures 7A, 7B:
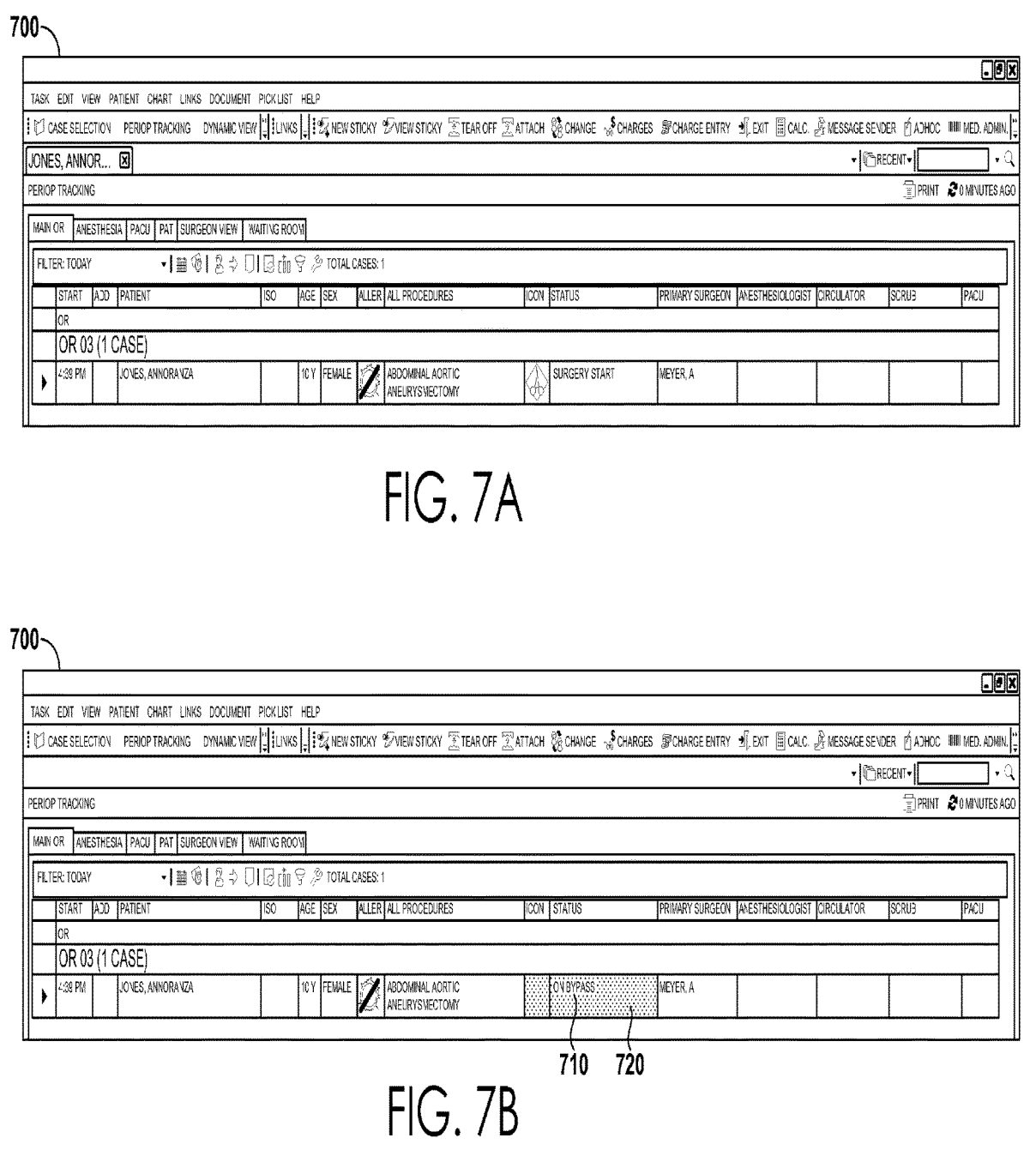

Similarly, the nurse needs to document the patient's current condition. The display 600 changes accordingly, as illustrated by FIG. 6B, to alert the nurse of the change in the patient's status. In this example, note 610 is displayed in the demographics bar. As illustrated by FIG. 7B, the perioperative tracking display 700 is also changed to reflect the change in the patient's status. In this example, the status 710 is updated to reflect the current status of the patient. In addition, the background color 720 of the status section is also changed to make it readily apparent to any clinician monitoring the status of the patient within this system.

As can be understood, the present invention provides systems, methods, and user interfaces for providing cloud rules and an alerting framework. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

The invention claimed is:

1. A method of causing display via a shared alerting framework, the method comprising:
    causing a first computing device to display a first user interface associated with a first patient;
    causing a second computing device to display a second user interface associated with the first patient, wherein the second user interface is different than the first user interface;
    detecting a trigger associated with a change in status of the first patient; and
    based at least in part on the detecting of the trigger, automatically causing the first computing device to modify at least a portion of the first user interface and automatically causing the second computing device to modify at least a portion of the second user interface, wherein the modifying of at least the portion of the first user interface and the second user interface indicates the change in status of the first patient.

2. The method of claim 1, wherein the modifying of at least the portion of the first user interface and the second user interface includes changing a background color and changing a size of the first patient's name.

3. The method of claim 1, wherein the modifying of at least the portion of the first user interface and the second user interface includes generating, in response to the detecting of the trigger, a note indicative of the change in status of the first patient.

4. The method of claim 1, wherein the first user interface includes a plurality of elements, and wherein a format of the plurality of elements do not change in response to the modifying of at least the portion of the first user interface.

5. The method of claim 1, wherein the first computing device does not include any applications that are integrated with any other application running on the second computing device except through a same alerting framework.

6. The method of 1, wherein the modifying of at least a portion of the first user interface includes locking a first application within the first computing device that is indicative of preventing a clinician from taking any action within the first application.

7. The method of claim 1, wherein the modifying of at least the portion of the first user interface ceases in response to one or more rules associated with the trigger no longer being met, the ceasing is indicative of the status of the first patient no longer being in a changed state.

8. One or more computer storage media having computer executable instructions embodied thereon, that when executed by one or more computing devices, cause the one or more computing devices to perform a method, the method comprising:
    causing a first display device to display a first user interface associated with a first application;

causing a second display device to display a second user interface associated with a second application, wherein the first display device and the second display device are associated to a same alerting framework in one or more healthcare information systems, and wherein the second application is a different application than the first application;

receiving indication that a trigger associated with one or more rules has been detected; and based at least in part on the received indication and the first display device and the second display device being associated to the same alerting framework, automatically causing the first display device to modify a display of at least a portion of the first user interface and automatically causing the second display device to modify a display of at least a portion of the second user interface.

9. The media of claim 8, wherein the modifying of the display of the first display device includes changing a workflow of the first application that is indicative of instructing a user to change one or more actions associated with treatment.

10. The media of claim 8, wherein the modifying of the display of the second display device includes generating, in response to the receiving of the indication of the detected trigger, a note indicative of the change in status of the first patient.

11. The media of claim 8, wherein the first user interface of the first display device includes a plurality of elements, and wherein the modifying of the display of the first display device includes changing indicia in a field within an element of the plurality of elements from first indicia to second indicia.

12. The media of claim 8, wherein the first application and the second application are not integrated except through the same alerting framework.

13. The media of claim 8, wherein the modifying of the display of the first display device includes locking the first application within the first display device that is indicative of preventing a clinician from taking any action within the first application, wherein the second application is not locked such that another clinician may take any action within the second application.

14. The media of claim 8, wherein the modifying of the display of the first display device ceases in response to the one or more rules no longer being met, the ceasing is indicative of the status of the first patient no longer being in a changed state.

15. A system comprising one or more processors coupled to one or more computer-storage devices, the computer-storage devices having stored thereon computer executable instructions that, when executed by the one or more processors, cause the one or more processors to perform a method, the method comprising:

causing display, within a first display device, a first user interface associated with a first application, wherein the first display device is one of a plurality of display devices included in a healthcare facility, and wherein the plurality of display devices are associated to a same alerting framework;

causing display, within a second display device of the plurality of display devices, a second user interface associated with a second application, wherein the first user interface is different than the second user interface;

receiving an indication that a trigger associated with one or more rules has been detected; and based at least in part on the receiving of the indication, automatically causing a modification of display of the first user interface within the first display device and causing a modification of display of the second user interface within the second display device.

16. The system of claim 15, wherein the modifying display includes changing a color of a background of a user interface associated with the first application.

17. The system of claim 15 wherein the modifying display includes generating, in response to the receiving of the indication that a trigger has been detected, a note indicative of the change in status of a first patient within the healthcare facility.

18. The system of claim 15, wherein the first user interface of the first display device includes a plurality of elements, and wherein the modifying display of the first display device includes changing color in a field within an element of the plurality of elements from a first color to a second color.

19. The system of claim 15, wherein the modifying display of the first display device includes locking the first application within the first display device that is indicative of preventing a clinician from taking any action within the first application.

20. The system of claim 15, wherein the modifying display of the first display device ceases in response to the one or more rules no longer being met, the ceasing is indicative of the status of a patient no longer being in a changed state.

* * * * *